US009968489B2

(12) United States Patent
Locke et al.

(10) Patent No.: US 9,968,489 B2
(45) Date of Patent: *May 15, 2018

(54) REDUCED-PRESSURE WOUND DRESSINGS

(71) Applicant: KCI Licensing, Inc., San Antonio, TX (US)

(72) Inventors: Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 262 days.

This patent is subject to a terminal disclaimer.

(21) Appl. No.: 14/656,439

(22) Filed: Mar. 12, 2015

(65) Prior Publication Data

US 2015/0230991 A1 Aug. 20, 2015

Related U.S. Application Data

(63) Continuation of application No. 13/554,572, filed on Jul. 20, 2012, now Pat. No. 8,992,510.

(60) Provisional application No. 61/514,801, filed on Aug. 3, 2011.

(51) Int. Cl.
*A61F 13/00* (2006.01)
*A61M 1/00* (2006.01)

(52) U.S. Cl.
CPC ..... *A61F 13/00068* (2013.01); *A61M 1/0088* (2013.01); *A61F 2013/00412* (2013.01)

(58) Field of Classification Search
CPC ............... A61F 13/00068; A61F 13/02; A61F 13/0216; A61M 1/00; A61M 1/0023; A61M 1/0058; A61M 1/0084; A61M 1/0088; A61M 27/00
See application file for complete search history.

(56) References Cited

U.S. PATENT DOCUMENTS

| 1,355,846 A | 10/1920 | Rannells |
| 2,547,758 A | 4/1951 | Kelling |
| 2,632,443 A | 3/1953 | Lesher |
| 2,682,873 A | 7/1954 | Evans et al. |

(Continued)

FOREIGN PATENT DOCUMENTS

| AU | 550575 B2 | 3/1986 |
| AU | 745271 B2 | 3/2002 |

(Continued)

OTHER PUBLICATIONS

European Search Report for corresponding EP15173724, dated Oct. 7, 2015.

(Continued)

*Primary Examiner* — Benjamin Klein

(57) ABSTRACT

Systems, methods, and dressings for treating a linear wound, such as an incision, on a patient are presented. The systems, dressings, and methods involve a sealed wound dressing assembly that helps form a fluid seal around the linear wound while simultaneously encompassing a subcutaneous delivery conduit to deliver fluid to or from a subcutaneous tissue site. In one instance, a reduced-pressure interface is used to allow the subcutaneous delivery conduit to pass through tissue at or near the linear wound and through a wound dressing assembly to a drainage receptacle.

30 Claims, 7 Drawing Sheets

(56) References Cited

U.S. PATENT DOCUMENTS

| | | |
|---|---|---|
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Canon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,992,510 B2 * | 3/2015 | Locke ................. A61M 1/0088 604/541 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0085795 A1 * | 4/2005 | Lockwood .......... A61M 1/0084 604/543 |
| 2006/0079852 A1 | 4/2006 | Bubb et al. |
| 2007/0055209 A1 * | 3/2007 | Patel ................. A61F 13/00063 604/315 |
| 2007/0219471 A1 | 9/2007 | Johnson et al. |
| 2010/0106106 A1 | 4/2010 | Heaton et al. |
| 2010/0191197 A1 * | 7/2010 | Braga ................ A61M 1/0088 604/313 |
| 2010/0268128 A1 * | 10/2010 | Randolph .......... A61F 13/00068 601/6 |
| 2011/0137270 A1 * | 6/2011 | Hu ..................... A61M 1/0088 604/319 |

FOREIGN PATENT DOCUMENTS

| | | |
|---|---|---|
| AU | 755496 B2 | 12/2002 |
| CA | 2005436 A1 | 6/1990 |
| CA | 2762889 A1 | 12/2010 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2007041642 A2 | 4/2007 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, 1997.

(56) References Cited

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

REDUCED-PRESSURE WOUND DRESSINGS

RELATED APPLICATIONS

This application is a continuation of U.S. patent application Ser. No. 13/554,572, filed Jul. 20, 2012, which claims the benefit, under 35 USC § 119(e), of the filing of U.S. Provisional Patent Application Ser. No. 61/514,801, entitled "Reduced-Pressure Wound Dressings," filed Aug. 3, 2011, which is incorporated herein by reference for all purposes.

BACKGROUND

The present disclosure relates generally to medical treatment systems and, more particularly, but not by way of limitation, to reduced-pressure dressings having a drain adapter and related systems, and methods for treating incisions.

Clinical studies and practice have shown that providing a reduced pressure in proximity to a tissue site can augment and accelerate the growth of new tissue at the tissue site. The applications of this phenomenon are numerous, but application of reduced pressure has been particularly successful in treating wounds. This treatment (frequently referred to in the medical community as "negative pressure wound therapy," "reduced-pressure therapy," or "vacuum therapy") provides a number of benefits, which may include faster healing and increased formulation of granulation tissue. Typically, reduced pressure is applied to tissue through a wound dressing assembly that includes a porous pad or other manifold device. The porous pad distributes reduced pressure to the tissue and channels fluids that are drawn from the tissue.

SUMMARY

According to an illustrative embodiment, a reduced-pressure system for treating a tissue site having a linear wound includes a dressing bolster formed from a medical bolster material. The dressing bolster is for placing on a patient's epidermis and is substantially sized to overlay the linear wound. The system further includes an over-drape for providing a fluid seal over the dressing bolster and a portion of the patient's epidermis, a reduced-pressure source, and a first reduced-pressure interface fluidly coupled to the dressing bolster and the reduced-pressure source. The first reduced-pressure interface is for delivering reduced pressure to the dressing bolster. The system also includes a reduced-pressure delivery conduit for fluidly coupling the reduced-pressure source and the first reduced-pressure interface. The system further includes a second reduced-pressure interface coupled to the over-drape, wherein the second reduced-pressure interface is sized and configured to receive a subcutaneous delivery conduit and to form a fluid seal about the subcutaneous delivery conduit.

According to another illustrative embodiment, a wound dressing assembly for treating a tissue site having a linear wound includes a dressing bolster having a first surface and a second, inward facing surface for deploying over a patient's epidermis and substantially sized to overlay the linear wound; an over-drape for providing a fluid seal over the dressing bolster and a portion of the patient's epidermis; and a first reduced-pressure interface operable to receive a reduced-pressure supply conduit. The assembly further includes an inner layer having a first surface and a second, inward-facing surface, and formed within a treatment-area aperture. The first surface of the inner layer is coupled at least in part to the second surface of the dressing bolster. A second-reduced-pressure interface includes an interface body formed with an aperture and having a first side and a second, patient-facing side. The aperture is sized to receive a subcutaneous delivery conduit and to form a fluid seal therewith. The second reduced-pressure interface is adapted to allow the subcutaneous delivery conduit to pass from a subcutaneous tissue site to an external site through the aperture. The subcutaneous delivery conduit is routed through the treatment-area aperture and the dressing bolster to the second interface.

According to another illustrative embodiment, a method of treating a tissue site having a linear wound includes applying a wound dressing assembly to the tissue site. The wound dressing assembly includes a dressing bolster formed from a medical bolster material that is shaped for placing on a patient's epidermis and substantially sized to overlay the linear wound, an over-drape for providing a fluid seal over the dressing bolster and a portion of the patient's epidermis, a first reduced-pressure interface fluidly coupled to the dressing bolster for delivering reduced-pressure to the dressing bolster, and a second reduced-pressure interface coupled to the over-drape, wherein the second reduced-pressure interface is sized and configured to receive a subcutaneous delivery conduit and to form a fluid seal between the subcutaneous delivery conduit and the wound dressing assembly. The method further includes fluidly coupling a reduced-pressure delivery conduit to a reduced-pressure source and the first reduced-pressure interface, delivering reduced pressure to the reduced-pressure delivery conduit, fluidly coupling a subcutaneous delivery conduit to the second interface, and delivering reduced pressure to the subcutaneous delivery conduit.

According to another illustrative embodiment, a method of manufacturing a wound dressing assembly for treating damaged subcutaneous damaged tissue includes providing a dressing bolster formed from a medical bolster material. The dressing bolster is for placing on a patient's epidermis and is substantially sized to overlay a linear wound. The method further includes providing an over-drape for providing a fluid seal over the dressing bolster and a portion of the patient's epidermis, providing a reduced-pressure source, providing a first reduced-pressure interface for delivering reduced pressure to the dressing bolster, providing a second reduced-pressure interface, and coupling the second reduced-pressure interface to the over-drape, wherein the second reduced-pressure interface is sized and configured to receive a subcutaneous delivery conduit and to form a fluid seal therebetween.

Other features and advantages of the illustrative embodiments will become apparent with reference to the drawings and the detailed description that follow.

BRIEF DESCRIPTION OF THE DRAWINGS

FIG. 6A is a detail of a portion of the wound dressing assembly of FIG. 6;

DETAILED DESCRIPTION OF ILLUSTRATIVE EMBODIMENTS

Figure 1:
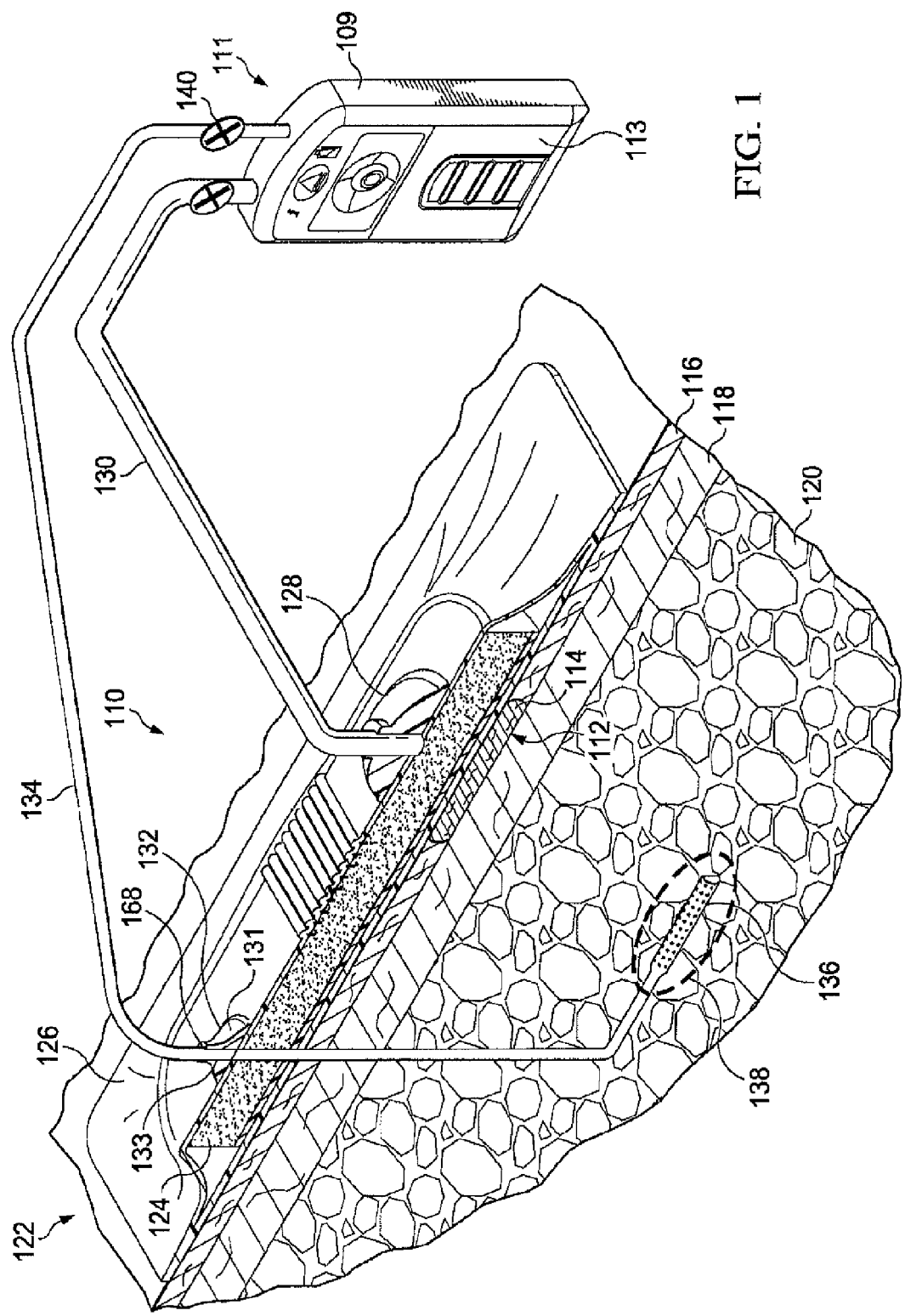
FIG. 1 is a schematic perspective view, with a portion shown in cross-section, of an illustrative reduced-pressure system for treating a tissue site having a linear wound that includes a first reduced-pressure interface and a second reduced-pressure interface.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

As a result of a surgery or other medical condition, a patient may have a subcutaneous wound that is located near or beneath a linear wound on the patient's epidermis. For example, after a surgery to remove subcutaneous tissue from a patient, the patient may have a linear wound as a result of the surgical incision. The patient may also have an area beneath their skin that will need to heal as a result of the surgery, i.e., a subcutaneous wound or defect.

In such a case, the subcutaneous wound may exude or collect fluids during the healing process, and a drain may be inserted at or near the end of the linear wound in order to collect exudates and prevent the collection of unwanted fluids at the tissue site of the subcutaneous wound. The drain may be connected to a drain tube, which may be referred to as a subcutaneous delivery conduit, that is configured to exit the patient's body at one end of the linear wound. The drain tube, which is a type of subcutaneous delivery conduit, may be connected to a drain for the purposes of collecting wound exudates in a sanitary fashion. Contemporaneously, a reduced-pressure treatment method may be applied to treat the linear wound that was caused during the surgery. The reduced-pressure treatment method involves the formation of a fluid seal over the treatment area that includes the linear wound.

The fluid seal is typically an important and fragile feature of a system that delivers reduced pressure to a wound site. Any breach in the fluid seal may cause a leak that may shut down or otherwise compromise a reduced-pressure delivery system because such systems tend to be highly intolerant of leaks. One method for providing the fluid seal may be to provide a wound dressing assembly that includes a pliable drape, or over-drape, that seals against the epidermis of the patient. By forming the fluid seal, the over-drape may preserve a pressure differential between the treatment area and the ambient environment, which may also be referred to as the external environment. As used throughout this document, the term "or" does not require mutual exclusivity. In cases where a drain tube is present, application of a reduced-pressure wound dressing assembly may be difficult because the drain tube may prevent the over-drape from sealing against the patient's epidermis. In cases where a treatment provider attempts to seal the treatment area by applying the over-drape over the drain tube, a leak may result. Further, even if a fluid seal can be obtained, movement of the drain tube may entirely disrupt the seal and cause a loss of reduced pressure at the treatment site, thereby compromising the ability to maintain the desired amount of reduced pressure at the tissue site. Thus, it is desirable to have a dressing assembly or interface for allowing a drain tube, or subcutaneous delivery conduit, to pass through a reduced-pressure treatment area (from a drain to a drain collection area) without disrupting the fluid seal between the treatment site and the ambient environment.

Referring now primarily to FIG. 1, an illustrative embodiment of a reduced-pressure treatment system 110 for treating a tissue site 112 that includes a linear wound 114, while simultaneously collecting wound exudates through a drain 136, is presented. The tissue site 112 is related to a linear wound 114. The tissue site 112 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 112 may include removal of fluids, e.g., exudate. The tissue site 112 is shown at epidermis 116, but in some cases may also involve the dermis 118, and subcutaneous tissue 120. The reduced-pressure treatment system 110 may also be used with other tissue sites.

The reduced-pressure treatment system 110 includes a wound dressing assembly 122 and a reduced-pressure subsystem 111. While the reduced-pressure treatment system 110 is shown in the context of a reduced-pressure wound dressing assembly 122 placed over a linear wound 114, it should be understood that the reduced-pressure treatment system 110 may be used on other tissue sites, including open wounds. The wound dressing assembly 122 includes a dressing bolster 124 that functions as a manifold, an over-drape 126, and a first reduced-pressure interface 128 to accommodate a reduced-pressure delivery conduit 130. The reduced-pressure delivery conduit 130 is fluidly coupled to the reduced-pressure subsystem 111.

Functionally, the reduced pressure developed by the reduced-pressure subsystem 111 is delivered through the reduced-pressure delivery conduit 130 to the first reduced-pressure interface 128. In one illustrative embodiment, the first reduced-pressure interface 128 is a T.R.A.C.® Pad or Sensa T.R.A.C.® Pad available from KCI of San Antonio, Tex. The first reduced-pressure interface 128 allows the reduced pressure to be delivered to the dressing bolster 124. In another embodiment, no reduced-pressure interface 128 is used. Instead, a lumen (or conduit) is placed through the over-drape 126 directly into the dressing bolster 124.

The wound dressing assembly 122 provides a fluid seal over an area that includes a tissue site 112 that is to be treated with reduced pressure. A fluid seal is a seal adequate to maintain reduced pressure at a desired site given the particular reduced-pressure source(s) or subsystem involved.

The wound dressing assembly 122 also includes a second reduced-pressure interface 132. The second reduced-pressure interface 132 is fastened to the over-drape 126 by an adhesive, bond, weld (e.g., an ultrasonic, thermal, or RF weld), or cement (not shown). The second reduced-pressure interface 132 maintains the integrity of the fluid seal over the tissue site 112 while allowing a subcutaneous delivery conduit 134 to pass through the dressing bolster 124 and over-drape 126. In an embodiment, the second reduced-pressure interface 132 comprises a molded plastic component that is welded or adhered to the over-drape 126.

The second reduced-pressure interface 132 of FIG. 1 is configured so that a user or treatment provider can exert a force against an outer surface of the second reduced-pressure interface 132 to route a subcutaneous delivery conduit 134 through the wound dressing assembly 122. At the same time, the user can press a subcutaneous delivery conduit 134 against the over-drape 126 at the location of the second reduced-pressure interface 132 with sufficient force to breach the over-drape 126. The second reduced-pressure interface 132 reinforces the over-drape 126 so that it can be breached without compromising the ability of the over-drape 126 to provide a fluid seal outside of the second reduced-pressure interface 132. In one embodiment, an aperture is formed in the over-drape at the second reduced-pressure interface 132 to facilitate a pathway through the wound dressing assembly 122.

The second reduced-pressure interface 132 may take any number of shapes and sizes. For example, the second reduced-pressure interface 132 may be shaped substantially as shown in FIG. 1, where the second reduced-pressure interface 132 includes flat top and bottom surfaces and an aperture 168. The aperture 168 may be sized to generate a radial compressive force against a subcutaneous delivery conduit 134 when the subcutaneous delivery conduit 134 is inserted through the second reduced-pressure interface 132. For example, an interference fit may be formed between the aperture 168 and the subcutaneous delivery conduit 134. According to one illustrative embodiment, the second reduced-pressure interface 132 may comprise a nipple 131 formed from an interface body 133 with the aperture 168 having an interior diameter $D_1$. The subcutaneous delivery conduit 134 may have an external diameter $D_2$. The diameters are related by the expression $D_1 < D_2$. $D_1$ is slightly less than $D_2$ whereby the fluid seal is formed by an interference fit. In another embodiment, $D_1$ may be equal to $D_2$.

The second reduced-pressure interface 132 may also be tapered such that the thickness of the second reduced-pressure interface 132 is increased at the aperture and gradually decreased to a minimal thickness at the outer edge. The thickness of the second reduced-pressure interface 132 may gradually increase from the edge to the boundary of the aperture 168 in a linear or curved manner. The second reduced-pressure interface 132 may also have a rounded, or dome-typed shape. Other shapes are possible as well.

The subcutaneous delivery conduit 134 functions to allow wound exudates to flow from a subcutaneous tissue site 138 from a drain 136. The subcutaneous delivery conduit 134 may fluidly couple to the reduced-pressure subsystem 111 or a second reduced-pressure subsystem (not shown). Thus, both the reduced-pressure delivery conduit 130 and subcutaneous delivery conduit 134 provide reduced pressure and may couple to the reduced-pressure subsystem 111. Here, the reduced-pressure delivery conduit 130 is coupled to the reduced-pressure subsystem 111 to apply reduced-pressure therapy to a tissue site 112. The subcutaneous delivery conduit 134 may also couple to the reduced-pressure subsystem 111, or to a separate reduced-pressure subsystem (not shown) to evacuate fluids, or exudates, from a drain 136.

Reduced pressure is a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Consistent with the use herein, unless otherwise indicated, an increase in reduced pressure or vacuum pressure typically refers to a relative reduction in absolute pressure.

In some embodiments, a different amount of reduced pressure may be desired at the tissue site 112 of the linear wound 114 than at the subcutaneous tissue site 138. In such embodiments, the subcutaneous delivery conduit 134 and reduced-pressure delivery conduit 130 may be fluidly coupled to different reduced-pressure sources and may include different fluid reservoirs associated with each. Alternatively, the delivery conduits 130, 134 may be coupled to the same reduced-pressure subsystem 111 through one or more pressure regulators 140 that allow a single reduced-pressure subsystem 111 to supply different amounts of reduced pressure to each conduit. In some embodiments, the same amount of reduced pressure may be desired at the tissue site 112 of the linear wound 114 as the subcutaneous tissue site 138. In these embodiments, the subcutaneous delivery conduit 134 and reduced-pressure delivery conduit 130 may be fluidly coupled to the same reduced-pressure source 109 without the need for pressure regulators.

Figure 2:
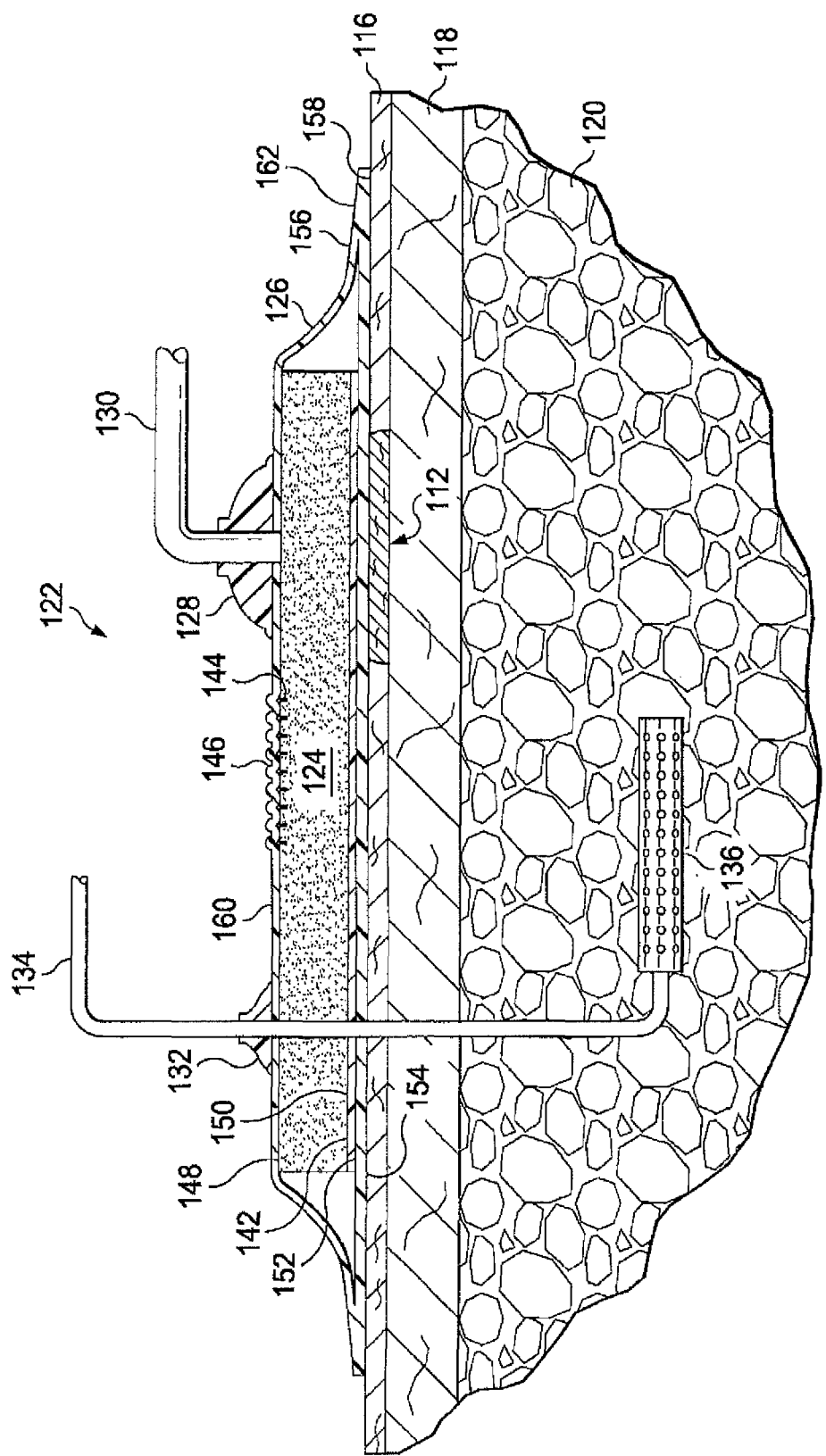
FIG. 2 is a schematic, cross-sectional view of the illustrative reduced-pressure system of FIG. 1.

Referring now primarily to FIG. 2, a side cross section of the wound dressing assembly 122 of FIG. 1 is presented. The wound dressing assembly 122 as shown includes an optional inner comfort layer 142 that may be coupled to the dressing bolster 124 and that lies between the dressing bolster 124 material and the epidermis 116 of a patient. The wound dressing assembly 122 may also include (latitudinal or longitudinal) flexibility notches 144 in order to add flexibility to the dressing bolster 124. Additionally, the over-drape 126 of wound dressing assembly 122 may include folds 146 or notches or ridges to add flexibility to the wound dressing assembly 122.

In addition to the first reduced-pressure interface 128 that is fluidly coupled to the reduced-pressure delivery conduit 130 and dressing bolster 124, the wound dressing assembly 122 also includes the second reduced-pressure interface 132. The second reduced-pressure interface 132 functions to accommodate the presence of a subcutaneous delivery conduit 134. The subcutaneous delivery conduit 134 functions as a drain tube that is fluidly coupled to a drain 136 without disturbing the ability of the reduced-pressure treatment system 110 to apply reduced pressure to a tissue site 112. The second reduced-pressure interface 132 fluidly couples a reduced pressure source to the drain 136 without causing a leak that hinders or stops the reduced-pressure therapy at tissue site 112.

The dressing bolster 124 of the wound dressing assembly 122 has a first side 148 and a second, inward-facing side 150. The dressing bolster 124 may be formed from any bolster material or manifold material that provides a vacuum space, or treatment space, such as a porous and permeable foam or foam-like material, a member formed with pathways, a graft, or gauze. As a more specific, non-limiting example, the dressing bolster 124 may be a reticulated, open-cell polyurethane or polyether foam that allows good permeability of wound fluids while under a reduced pressure. One such foam material that has been used is a VAC® GranuFoam® material available from Kinetic Concepts, Inc. (KCI) of San Antonio, Tex. Any material or combination of materials may be used for the manifold material provided that the manifold material is operable to distribute the reduced pressure.

A manifold is generally a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels. In some embodiment, the manifold may be formed by a plurality of layers or substrates. Moreover, in some embodiments of the manifold with multiple layers, the layer that is closest to the patient during use may be the least hydrophilic and the most hydrophobic material.

The reticulated pores of the GranuFoam® material are helpful in carrying out the manifold function, but again other materials may be used. A material with a higher, or lower, density (smaller pore size) than GranuFoam® material may be desirable in some situations. Among the many possible materials, the following may be used: GranuFoam® material, Foamex® technical foam (www.foamex.com), gauze, a flexible channel-containing member, a graft, etc. In some instances it may be desirable to add ionic silver to the foam in a micro-bonding process or to add other substances to the material, such as antimicrobial agents.

The manifold typically includes a plurality of flow channels or pathways that distribute fluids provided to and removed from the tissue site around the manifold. Here, the manifold may be a biocompatible material that is capable of being placed in contact with the subcutaneous tissue site and distributing reduced pressure to the subcutaneous tissue site. The manifold material may include a bioresorbable material that may remain in a patient's body following the reduced-pressure treatment. Generally, the bioresorbable material is a material that enzymatically or chemically degrades into a simple chemical species in vivo, and which may be removed from the body by excretion of metabolism. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold material may further serve as a scaffold for new cell-growth, or a scaffold material may be used in conjunction with the manifold material to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 6:
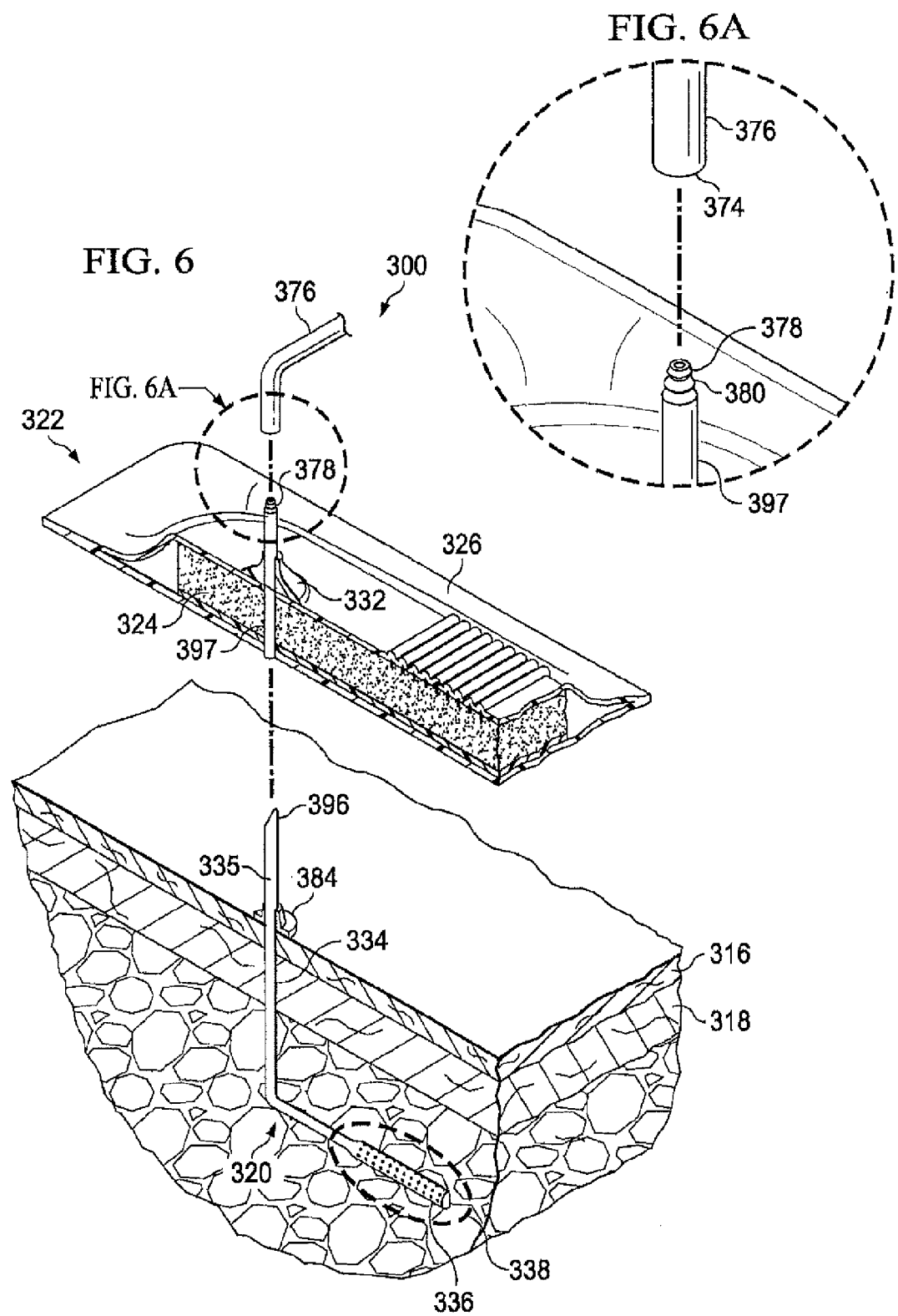
FIG. 6 is a partially-exploded, schematic perspective view, with a portion in cross-section, of an illustrative embodiment of a wound dressing assembly having a second reduced-pressure interface.

In one illustrative embodiment, the dressing bolster 124 is manufactured as follows. A foam block of Granufoam® material, e.g., 1.21 meter×1.8 meter×0.5 meter block, is cut to have a 19 mm height, and a saw is used to form lateral grooves, or lateral flexibility notches as shown in FIGS. 2 and 6. Then, a dry layer, which may be the inner comfort layer 142, is laminated or attached onto the second, or bottom, surface. The foam block is then cut using a die cut to form individual dressing bolsters 124.

The optional inner comfort layer 142 has a first side 152 and a second, inward-facing side 154. The first side 152 of the optional inner comfort layer 142 may be coupled, for example, by a heat bond or any other technique, to the second, inward-facing side 150 of the dressing bolster 124. The inner comfort layer 142 typically provides for patient comfort when the dressing bolster 124 is placed adjacent to the patient's epidermis 116. The inner comfort layer 142 may be any material that helps prevent skin irritation and discomfort while allowing fluid transmission through the inner comfort layer 142. As non-limiting examples, a woven, elastic material or a polyester knit textile substrate may be used. As another non-limiting example, an InterDry™ textile material from Milliken Chemical, a division of Milliken & Company, Inc. of Spartanburg, S.C., may be used. The inner comfort layer 142 may include anti-microbial substances, such as silver, and may be made like a breathable, dry layer.

The dressing bolster 124 may include a plurality of flexibility notches 144 or recesses that may be lateral cuts in the dressing bolster 124 on the first side 148. In addition, the flexibility notches 144 may be one or more longitudinal notches, or longitudinal cuts, or other cuts. The cuts may be made using a saw (or notched blade), a hot knife, or other device. The flexibility notches enhance flexibility of the dressing bolster 124. The enhanced flexibility may be particularly useful when the wound dressing assembly 122 is applied over a patient's joint area or another area of movement. For example, if the dressing bolster 124 is used on a knee, the dressing bolster 124 may need to flex or extend as much as 100% or more and the flexibility notches help provide the desired flexibility. The flexibility notches may also take various shapes, such as hexagons, slits, or squares.

The dressing bolster 124 may be formed with lateral edges that are orthogonal with respect to the second, inward-facing side 150 of the dressing bolster 124. The lateral edges may also be formed with a beveled edge or angled edge. The angled or beveled edge may distribute shear stress between the dressing bolster and the patient's epidermis 116. The dressing bolster 124 may also have rounded sides. The dressing bolster 124 may have a small aperture, or cut, formed through the bolster to lead the subcutaneous delivery conduit 134 through the dressing bolster 124 with relatively less force.

A sealing member, which is shown as the over-drape 126, provides a fluid seal over the dressing bolster 124 and at least a portion of the patient's epidermis 116. As such, the over-drape 126 may be formed from any material that allows for a fluid seal. The over-drape 126 may be sealed against epidermis 116 or against a gasket material by a sealing apparatus, such as a pressure-sensitive adhesive.

The sealing apparatus may take numerous forms, such as an adhesive sealing tape, or drape tape or strip; double-side drape tape; pressure-sensitive adhesive; paste; hydrocolloid; hydrogel; or other sealing means. As discussed herein, the sealing member is commonly an over-drape 126. If a tape is used, the tape may be formed of the same material as the over-drape 126 with a pre-applied, pressure-sensitive adhesive. The pressure-sensitive adhesive may be applied on a second, inward-facing side 158 of the over-drape 126 or portion thereof. The pressure-sensitive adhesive helps provide a fluid seal between the over-drape 126 and the epidermis 116. As used herein, the fluid seal may also include a gasket against the epidermis 116. Before the sealing member is secured to the epidermis, removable strips, or release liners, covering the pressure-sensitive adhesive may be removed.

The sealing member, or over-drape 126, may be an elastomeric material or any material or substance that provides a fluid seal. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, sealing member materials may include a silicone drape, 3M Tegaderm® drape, acrylic drape such as one available from Avery Dennison, or an incise drape.

The sealing member, or over-drape 126, may include a first sealing member or drape portion 160 and a second sealing member or drape portion 162. The first sealing drape portion 160 extends over the first side 148 of the dressing bolster 124. The over-drape 126 extends further to form a sealing member flange, or sealing member extension, which has a first side and a second, inward-facing side (not explicitly shown). An aperture (not explicitly shown but analogous to 559 in FIG. 8) is formed on a portion of the over-drape 126 to allow fluid communication with a first reduced-pressure interface 128, which is fluidly coupled to the reduced-pressure subsystem 111.

The second, inward-facing side of the over-drape extension is placed on a first side (top side for the orientation of FIG. 1) of the second sealing drape portion 162 and coupled, such as by an adhesive, bond, welding (e.g., ultrasonic, thermal or RE welding), or cements (not shown). Alternatively, the first sealing drape portion 160 and second sealing drape portion 162 may be integrally formed. The first sealing drape portion 160 may include a plurality of folds 146, or stretch zones. The folds 146 allow additional drape material to become available, to stretch, or to move, if needed. For example, if the wound dressing assembly 122 is used on a joint, when the joint is flexed, additional drape material may be to useful accommodate movement of the joint. The folds 146 facilitate such movement.

Prior to application, one or more release members (not shown but analogous to 581 and 583 in FIG. 8) may be releasably coupled to the first side of the second sealing drape portion 162. The release members provide stiffness and help during deployment of the wound dressing assembly 122. The release members are typically either casting paper or a film held on the first side of the second sealing drape portion 162.

The reduced-pressure subsystem 111 includes at least one reduced-pressure source 109, which can take many different forms. The reduced-pressure source 109 provides reduced pressure as a part of the reduced-pressure treatment system 110. The reduced-pressure source 109 is fluidly coupled to the first reduced-pressure interface 128 by the reduced-pressure delivery conduit 130.

The reduced-pressure subsystem 111 may have one or more of a reservoir regions 113 or canister regions. The reservoir region 113 or canister region may include one or more filters to protect the pneumatic system from the ingress of liquids from the tissue site 112 or subcutaneous tissue site 138. An interposed membrane filter, such as a hydrophobic or oleophobic filter, may be interspersed between the reduced-pressure delivery conduit 130 and the reduced-pressure subsystem 111. One or more devices may be fluidly coupled to the reduced-pressure delivery conduit 130 in addition to the reduced-pressure subsystem 111. For example, another fluid reservoir or collection member to hold exudates and other fluids removed, a pressure-feedback device, a volume detection system, a blood detection system, an infection detection system, a flow monitoring system, or a temperature monitoring system may be coupled to the reduced-pressure delivery conduit 130. Such devices may be included in or formed integrally to the reduced-pressure subsystem 111.

The reduced-pressure subsystem 111 may be any device for supplying a reduced pressure, such as a vacuum pump, wall suction, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The reduced pressure developed by reduced-pressure subsystem 111 is delivered through the reduced-pressure delivery conduit 130 to the first reduced-pressure interface 128. The first reduced-pressure interface 128 allows the reduced pressure to be delivered through the over-drape 126 to the dressing bolster 124.

In providing treatment with the reduced-pressure treatment system 110, it may be desirable to know that reduced pressure of at least a certain threshold level is being delivered to the tissue site 112. A dressing reduced-pressure indicator coupled to the reduced-pressure source can accomplish this task. The dressing reduced-pressure indicator may, also be a separate unit fluidly coupled to the over-drape 126 such that pressure from within the sealed space of the over-drape 126 reaches the dressing reduced-pressure indicator or may be associated with the first reduced-pressure interface 128 as part of the reduced-pressure subsystem 111. When adequate reduced pressure is present, the reduced-pressure indicator may assume a collapsed position and when inadequate reduced pressure is present the reduced-pressure indicator may assume a non-collapsed position.

Figure 3A:
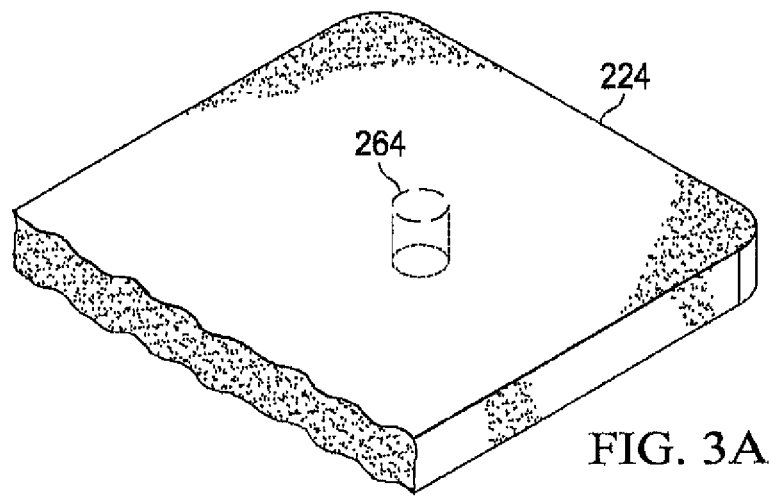
FIG. 3A is a schematic, perspective view of a portion of an illustrative dressing bolster that forms a part of a reduced-pressure system.

In some embodiments, the dressing bolster 124 is pre-formed to accommodate the presence of a subcutaneous delivery conduit 134 that may or may not be present. As shown in FIG. 3A, a dressing bolster 224 may be pre-formed to optionally receive a subcutaneous delivery conduit by the formation of a relieved area such as a perforated cut 264 or perforated cylinder of bolster material. To allow for easy passage of the conduit through the dressing bolster, the perforated cylinder of bolster material can be removed or punched out of the dressing bolster 224 by hand when a drain is to be applied. Additionally, it may be desirable to perforate the bolster material with multiple cuts of various diameters so that a piece of bolster material that is approximately the size of any foreseeable drain tube size can be removed by hand.

Figure 3B:
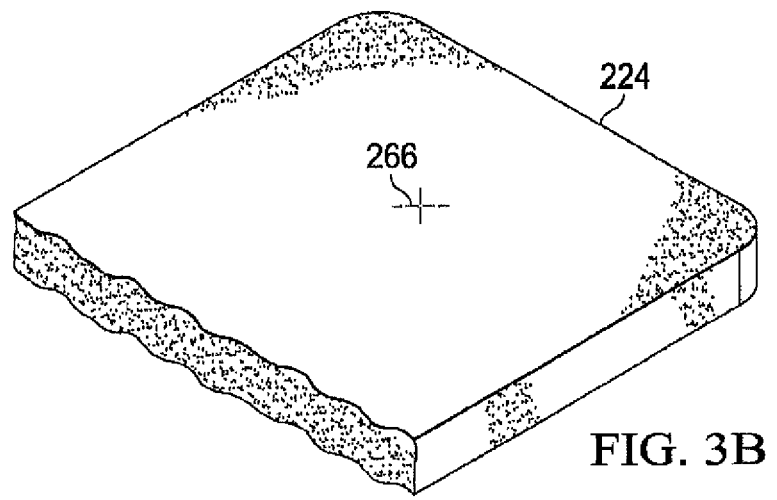
FIG. 3B is a schematic, perspective view of a portion of an illustrative dressing bolster that forms a part of a reduced-pressure system.

Alternatively, where slightly more deformation in the dressing bolster 224 is tolerable, the dressing bolster 224 may have a relieved area in the form of a cross-cut 266 made in the bolster material as shown in FIG. 3B to allow for the passage of a drain tube. The perforated cut 264 may be any variety of perforated shapes or sizes depending on the type of conduit or tubing to be routed through the dressing bolster 224. In cases where the dressing bolster 224 is assembled with an optional comfort layer, such as inner comfort layer 142 of FIG. 2, the perforation or cross-cut may also be formed in the inner comfort layer 142 to complement the perforated cut 264 or cross-cut 266 in the dressing bolster material.

Figure 4:
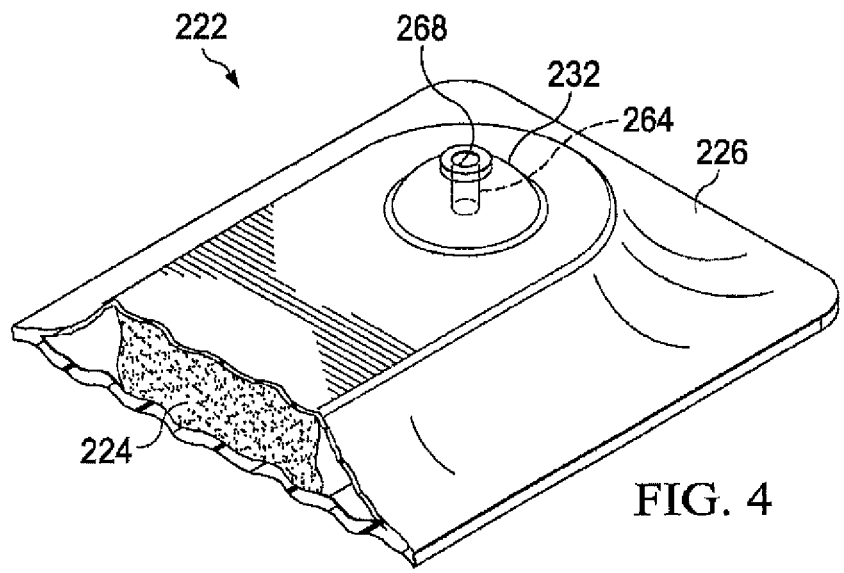
FIG. 4 is a schematic, perspective view of a portion of a wound dressing assembly for treating a tissue site having a linear wound.

Referring now primarily to FIG. 4 a wound dressing assembly 222 that incorporates a dressing bolster 224 having a relieved area is shown. The wound dressing assembly 222 components may have a perforated cut 264 or cross-cut 266 (FIG. 3B) to allow for the easy removal of a cylinder of dressing bolster material in order for a subcutaneous delivery conduit to pass through the dressing bolster 224. In such embodiments, the perforated cut 264 or cross-cut 266 may extend through only part of the wound dressing assembly so that a fluid seal is maintained at a tissue site whether or not a subcutaneous delivery conduit is present. The wound dressing assembly includes a second reduced-pressure interface 232 to form a fluid seal at the boundary of the second reduced-pressure interface 232 and subcutaneous delivery conduit if one is present. The second reduced-pressure interface 232 may function to reinforce the seal provided by the over-drape 226 between a tissue site and the ambient environment. Here, the second reduced-pressure interface 232 also includes an aperture 268 for allowing a section of conduit to be routed through the second reduced-pressure interface 232.

Figure 5:
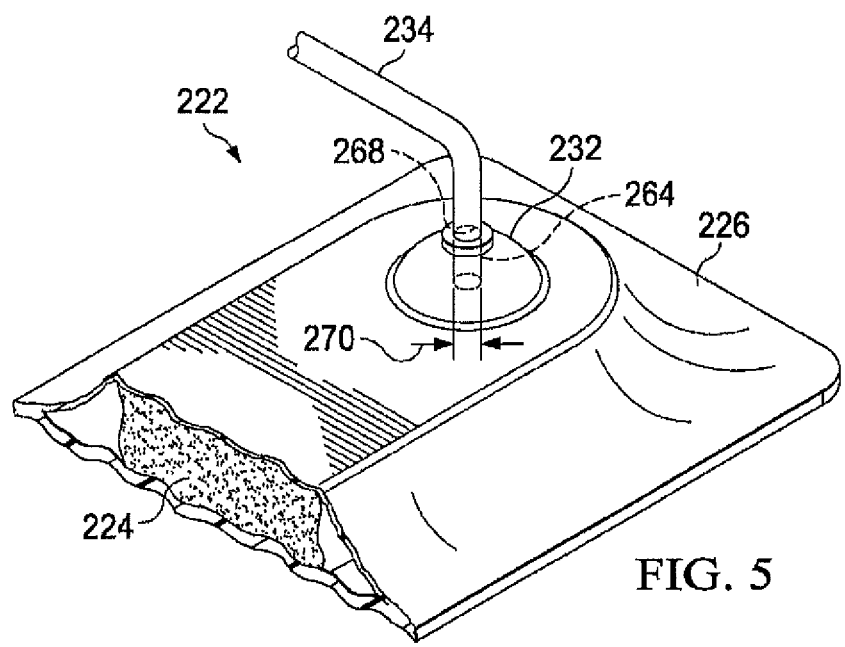
FIG. 5 is a schematic, perspective view of a portion of a wound dressing assembly for treating a tissue site having a linear wound.

Referring now primarily to FIG. 5, the second reduced-pressure interface 232 may be molded using a material with elastomeric properties, i.e., an elastomer, as discussed above. The elasticity of the material of the second reduced-pressure interface 232 enables the aperture 268 in the second reduced-pressure interface 232 to expand to allow a section of conduit, or subcutaneous delivery conduit 234 to pass through the aperture 268. In one embodiment, the aperture 268 may be of a slightly smaller diameter than the diameter of the conduit that may route through the second reduced-pressure interface 232. This slight overlap in sizing may achieve an interference fit that causes the aperture 268 to undergo a small amount of deformation when a subcutaneous delivery conduit 234 is routed through the second reduced-pressure interface 232.

As a result of the deformation, elastomeric properties (i.e., elasticity) of the second reduced-pressure interface 232 may generate a radial compressive force 270 between the surface of the aperture 268 and the subcutaneous delivery conduit 234. The radial compressive force 270 may thereby foam a fluid seal at the boundary of the second reduced-pressure interface 232 and subcutaneous delivery conduit 234, thereby preserving the pressure differential between the tissue site and the ambient environment. In some cases, additional materials may be used to form or strengthen this sealed boundary of the second reduced-pressure interface 232 and the subcutaneous delivery conduit 234. For example, adhesives or one or more gaskets (for example, an o-ring) may be installed between the surface of the aperture 268 and the outer surface of the subcutaneous delivery conduit 234 to enhance the strength of the fluid seal.

Referring now primarily to FIG. 6, another embodiment of a reduced-pressure system 300 for treating a tissue site having a linear wound (not shown) is presented. The reduced pressure system 300 includes second reduced-pressure interface 332 that is incorporated into a wound dressing assembly 322 to be applied to a tissue site (not shown). The tissue site is proximate to a first conduit segment 335 of the subcutaneous delivery conduit 334. In some cases, it may be desirable to allow the first conduit segment 335 of subcutaneous delivery conduit 334 to remain installed in subcutaneous tissue 320 and to apply a wound dressing assembly 322 over the inserted conduit while disturbing the surrounding tissue as little as possible. Here, a more modular solution is shown for applying a wound dressing assembly 322 to deliver reduced pressure to a linear wound (not shown) that is located near the point in the patient's epidermis where the subcutaneous delivery conduit 334 exits the patient's epidermis or skin.

The subcutaneous delivery conduit 334 may include a first conduit segment 335 that extends only a small distance (e.g., about 10 centimeters) above a patient's epidermis 316 and that is subsequently coupled to additional sections of conduit, e.g., second segment 376 or adapter 397. The combined conduit segments 335, 397, and 376 (or in some embodiments, 335 and 376) are used to evacuate collected fluids. The first conduit segment 335 of the subcutaneous delivery conduit 334 may remain installed in the patient and be sized, trimmed, or otherwise configured to protrude from the epidermis 316 enough to allow a sealed coupling between an end portion 396 of the first conduit segment 335 and an end portion 374 of a second conduit segment 376. The second conduit segment 376 may be fluidly coupled to a reduced-pressure source and drainage collection area (not shown). The second conduit segment 376 of the subcutaneous delivery conduit 334 may be removed and replaced without removing the first conduit segment 335.

The coupling between the first conduit segment 334 and second conduit segment 376 may occur in a number of ways. For example, an effective coupling may be achieved by providing an interference fit between the end portion 335 of the first conduit segment 334 to the second conduit segment 376. This coupling may be a direct coupling or a coupling made using the adapter 397, or coupler, that includes an intermediate conduit segment. If an adapter 397 is not used, the first conduit segment may be sized to protrude through the wound dressing assembly 322 and the second reduced-pressure interface 332, and the end portion (or distal end) 374 of the second conduit segment 376 may be sized to fit snugly over the end portion 396 of the first conduit segment 335. The overlap of conduit segments (335 and 376) forms a liquid-tight seal.

The adapter 397 may be a coupler having tapered conduit ends adapted to form fluid seals with both the first conduit segment 335 and second conduit segment 376. Any sealing means used to couple the adapter 397 to the first conduit segment 335 and second conduit segment 376 may alternatively be used to couple the first conduit segment 335 directly to the second conduit segment 376. For example, overlapping portions of the first conduit segment 335 and second conduit segment 376 may be forced together to form the coupling. Additionally, the second conduit segment 376 may receive a grooved conduit segment 380 on the end segment 378 of the adapter 397, as suggested in FIG. 6A, or a grooved segment of the first conduit segment 335. The end portions of the conduit segments may also include other physical features to aid in forming and preserving a seal. For example, the outer surface of a smaller conduit portion may be angled, or tapered and the inner surface of a larger diameter conduit portion may have complementary grooves or a taper to receive and seal against the opposing conduit segment.

A securing member 384 may be optionally included to secure the first conduit segment 335 relative to the epidermis 316 to minimize irritation of the surrounding tissue during the application of the dressing assembly 322. As such, a securing member 384 may be of a low hardness material that is very flexible and transmissive to moisture to substantially eliminate or reduce irritation and damage to the underlying dermis. The securing member 384 material may be porous material, such as a sintered rubber or silicone polymer member. A securing member 384 may adhere to the epidermis 316 using an adhesive or other attachment device. The securing member 384 helps secure the first conduit segment 335 in order to prevent unwanted movement of the first conduit segment 335. The securing member 384 may take the shape of a ring, or may have a flanged shape as shown in FIG. 6. In such an arrangement, the securing member 384 may function as an intermediate conduit segment and form a sealed coupling between the first conduit segment 334 and second conduit segment 376 or may be a pass through device that only secures the conduit segments 335 and 376.

Figure 7:
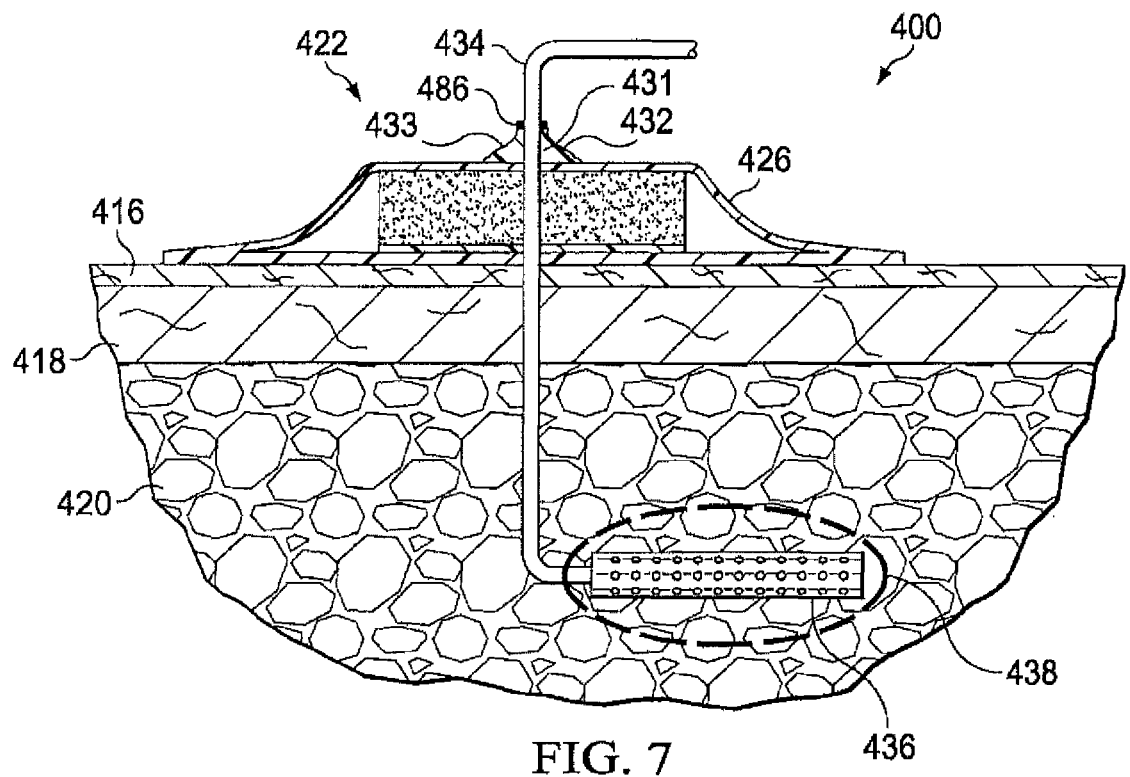
FIG. 7 is a schematic, side cross-sectional view of an illustrative reduced-pressure system for treating a tissue site having a linear wound and providing a subcutaneous delivery conduit to a subcutaneous tissue site.

Referring now primarily to FIG. 7, another reduced-pressure system 400 for treating a tissue site having a linear wound is presented that includes a second reduced-pressure interface 432. A wound dressing assembly 422 is analogous to the wound dressing assembly 122 of FIG. 2 in many respects. However, the over-drape 426 is more loose fitting and can be formed over the second reduced-pressure interface 432 and secured against the subcutaneous delivery conduit 434 with an o-ring 486 or clamp. The second reduced-pressure interface 432 may include a nipple 431 formed from an interface body 433.

Figure 8:
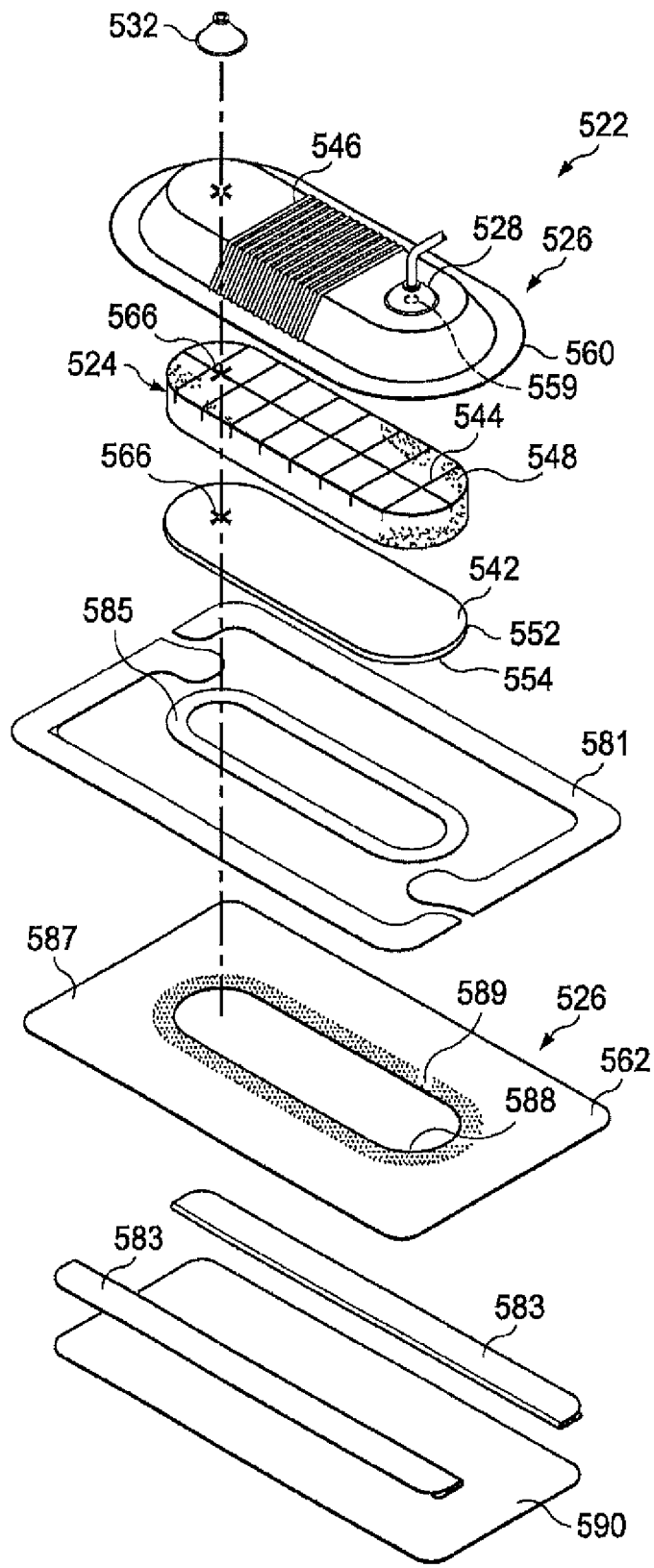
FIG. 8 is a schematic, exploded, perspective view of an illustrative embodiment of a wound dressing assembly that includes a second reduced-pressure interface.

Referring now primarily to FIG. 8, an exploded perspective view of a portion of a wound dressing assembly 522 for application in treating a tissue site with reduced pressure is presented. The tissue site may be a subcutaneous tissue site, a linear wound, area wound, or other wound or graft. The wound dressing assembly 522 presented in FIG. 8 is shown in a pre-deployment state and in an exploded view. The wound dressing assembly 522 is analogous in most respects to the wound dressing assembly 122 and of FIGS. 1 and 2. To indicate corresponding parts, the reference numerals have been indexed by 100 and may not be further mentioned.

The wound dressing assembly 522 includes a dressing bolster 524, which in turn may include flexibility notches 544 in both the lateral and longitudinal directions relative to the surface of the dressing bolster 524. The first side 548 of the dressing bolster 524 is covered by an over-drape 526, which may include a first drape portion 560 and a second drape portion 562. The first drape portion 560 includes folds 546 and a drape aperture 559. The second drape portion 562 is formed with a treatment area aperture 588 that provides an opening for at least a portion of the dressing bolster 524 or an inner comfort layer 542 to be applied directly against a patient's epidermis. The second drape portion 562 has first side 587 and has an adhesive 589 applied on a portion of the first side 587. The adhesive 589 is used primarily during manufacture to hold the dressing bolster 524 (or inner comfort layer 542 if present) against the second drape portion 562 during assembly and also used to help hold the dressing bolster 524 during use. Before applying the dressing bolster 524 or inner comfort layer 542 against the adhesive 589, the adhesive 589 is covered by a center releasable member 585. Outboard of the adhesive 589 on the first side 587 are releasable members 583 that provide stiffness to the over-drape 526 during deployment.

The second, inward-facing side (not explicitly shown but opposite side of the first side 587) of the second drape portion 562 may be covered with an adhesive. In the pre-deployment state, this adhesive is covered by a bottom release member 590 and side release members 583.

Once assembled, the wound dressing assembly 522 may resemble the dressing assembly 122 of FIG. 1. The use and design may vary, but in one illustrative embodiment, the wound dressing assembly 522 may deployed as described below. A subcutaneous delivery conduit (not shown) may be inserted into the patient and then a distal end placed through the wound dressing assembly 522 from a second side to the first side. In one embodiment, the subcutaneous delivery conduit is pushed through preformed cuts 566 in the comfort layer 542 (if present) and optionally through the dressing bolster 524.

The bottom release liner 590 is removed and exposed adhesive on the second, inward-facing side of the second drape portion 562 is placed against a portion of the patient's epidermis beginning at one end and the wound dressing assembly 522 may be placed over a linear wound. After smoothly applying the second drape portion 562, the side release members 583 are removed. The release members 581 on the first side 587 of the over-drape 526 are removed. A first reduced-pressure interface 528 is coupled to the drape aperture 559 in the first drape portion 560. A second reduced-pressure interface 532 may also be adhered to the drape (if not already applied during manufacture) at a location that is coaxial with the center of pre-formed cuts 566 made in the dressing bolster 524 and inner comfort layer 542 (if present) to accommodate the presence of a drain. The center release member 585 would have been removed during manufacture.

A user or treatment provider may apply the wound dressing assembly 522, that includes the second reduced-pressure interface 532 with the drain or other subcutaneous delivery tube within the footprint of the wound dressing assembly 522. In one embodiment, the second reduced-pressure interface is installed in the wound dressing assembly during manufacture. In another embodiment, the second reduced-pressure interface 532 is a separate item that may be added at the time of use. For example, a drain tube may protrude from the end of a surgical wound and therefore a user would recognize that the second reduced-pressure interface 532 is desired and apply the second reduced-pressure interface 532.

In the application of one embodiment, after selecting the wound dressing assembly, the user would orient the wound dressing assembly 522 such that pre-formed cuts 566 in the dressing bolster are aligned with the subcutaneous delivery conduit of the drain. The user would then press the conduit through the dressing bolster until the user felt the resistance of the over-drape 526. The user would apply a force to the molded reduced-pressure interface to push the conduit through the drape, which breaches when subjected to a critical force. In order to apply the critical force, the reduced-pressure interface may need to be of an adequate size for a user to grip the material that forms the interface and press it against the conduit. For example, the second reduced-pressure interface may need to extend for at least one centimeter radially past the aperture through which the conduit passes. The user would then draw a sufficient amount of conduit through the wound dressing assembly 522 to allow for the placement of the wound dressing assembly 522 before connecting the conduit to a receptacle.

This method of application should result in both the second reduced-pressure interface and the breached over-drape exerting radial compression about the conduit to form a fluid seal at the border of the conduit and wound dressing assembly 522.

In a similar embodiment, the second reduced-pressure interface 532 may be added at the time of deployment. In cases where a subcutaneous delivery conduit is present near the wound site, the conduit may be routed through pre-formed cuts 566, or through similar newly formed cuts. Similarly, a distal end of the conduit may be pressed through a portion of the over-drape 526 that is designed to be punctured or through a newly formed incision in the drape. The second reduced-pressure interface 532 may be placed over the distal end of the subcutaneous delivery conduit, slid over the subcutaneous delivery conduit, and adhered to the outer surface of the over-drape 526. The distal end of the subcutaneous conduit may then be coupled to a reduced pressure source. A reduced-pressure delivery conduit may couple first reduced-pressure interface 528 to a reduced-pressure source. The reduced-pressure source may be the same for both interfaces, or different reduced-pressure sources may be attached to each interface as desired.

Figure 9:
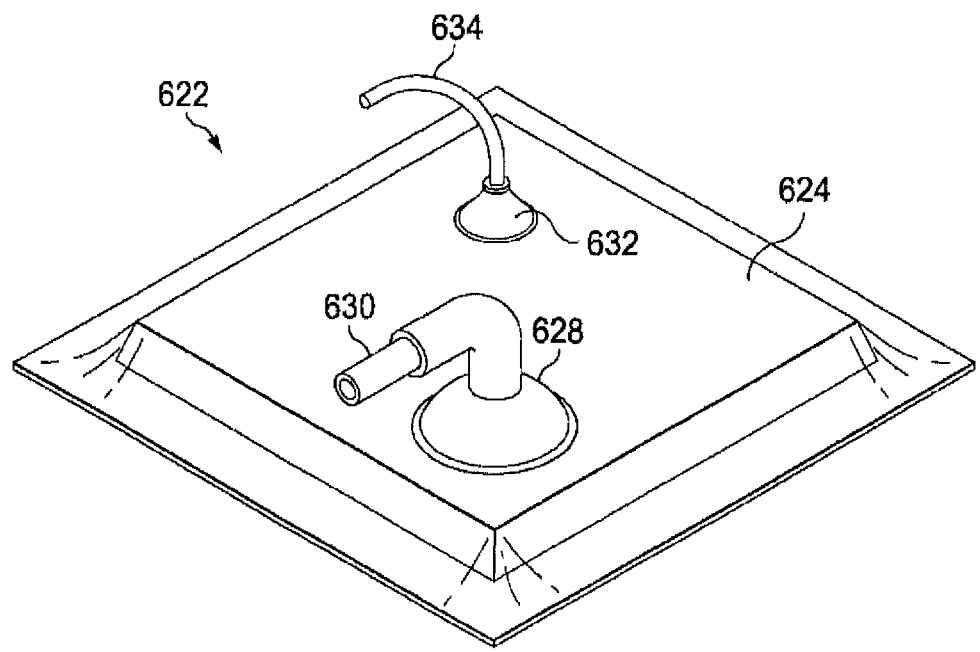
FIG. 9 is a schematic, perspective view of an illustrative embodiment of a wound dressing assembly having a first reduced-pressure interface and a second reduced-pressure interface.

Referring now primarily to FIG. 9, a dressing assembly 622 having an alternative shape is shown. The dressing assembly 622 may be sized and configured to apply reduced pressure to different portions of the body and may vary in size and shape accordingly. Similarly, the size of the dressing assembly 622 may vary in accordance with the anticipated wound size. Here, the dressing assembly 622 is shown having many of the features and attributes discussed above, including dressing bolster 624, a first reduced-pressure interface 628, a first reduced-pressure conduit 630, a second reduced-pressure interface 632, and a subcutaneous delivery conduit 634.

In addition to facilitating a pathway for a drain tube, the second reduced-pressure interface 632 may also function to deliver additional treatment and diagnostic applications to the wound site. For example, in addition to accommodating a drain, the second subcutaneous delivery conduit 634 may be used to monitor the wound site using a small wire sensor attached to an external diagnostic device. Similarly, the second reduced-pressure interface 632 may allow for the application of reduced-pressure therapy at a closely located subcutaneous wound site. In such an application, the subcutaneous delivery conduit 634 can be used to deliver a manifold material to a subcutaneous tissue site such as bone injury, to which the manifold material and subcutaneous delivery conduit can be fluidly coupled.

After delivering the manifold material, the subcutaneous delivery tube 634 may be coupled to a reduced-pressure source (not shown) to deliver reduced pressure to the subcutaneous tissue site, such as a bone or spinal injury. As such, the addition of the second reduced-pressure interface 632 provides for the delivery of reduced-pressure therapy to two distinct tissue sites using a single wound dressing assembly and reduced-pressure source.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure system, comprising:
   a dressing bolster adapted for placing on an epidermis and comprising a plurality of flexibility notches;
   an over-drape adapted for providing a fluid seal over the dressing bolster and a portion of the epidermis;
   a first reduced-pressure interface adapted to be fluidly coupled to the dressing bolster; and
   a second reduced-pressure interface coupled to the over-drape and fluidly coupled to the dressing bolster, wherein the second reduced-pressure interface is sized and configured to receive a subcutaneous delivery conduit and to form a fluid seal about the subcutaneous delivery conduit.

2. The reduced-pressure system of claim 1, further comprising a pre-formed pathway for routing the subcutaneous delivery conduit through the dressing bolster and the over-drape.

3. The reduced-pressure system of claim 1, wherein the second reduced-pressure interface comprises a nipple with an aperture having an interior diameter $D_1$, wherein the subcutaneous delivery conduit has an external diameter $D_2$, and wherein $D_1 < D_2$ whereby the fluid seal is formed.

4. The reduced-pressure system of claim 1, wherein the dressing bolster has a first surface and a second surface for deploying over the epidermis; and further comprising:
   an inner layer having a first surface and a second surface, and formed with a treatment-area aperture, and wherein the first surface of the inner layer is coupled at least in part to the second surface of the dressing bolster, wherein the inner layer is pre-cut to receive the subcutaneous delivery conduit.

5. The reduced-pressure system of claim 1, wherein the second reduced-pressure interface comprises one or more o-rings.

6. The reduced-pressure system of claim 1, further comprising:
   a subcutaneous delivery conduit comprising a first conduit segment and a second conduit segment; and
   wherein the second reduced-pressure interface comprises an adapter that is sized and configured to:
   receive an end portion of the first conduit segment;
   receive an end portion of the second conduit segment; and maintain a fluid coupling between the first conduit segment and the second conduit segment.

7. The reduced-pressure system of claim 1, wherein the second reduced-pressure interface comprises a molded elastomer having:
   a first surface;
   a second surface;
   an aperture sized to receive the subcutaneous delivery conduit and generate a compressive force against the subcutaneous delivery conduit; and
   an adhesive for forming a fluid seal between the second surface and the over-drape.

8. The reduced-pressure system of claim 7, wherein the second reduced-pressure interface is sized to transfer a hand-generated force equal to an amount of force required to puncture the over-drape with the subcutaneous delivery conduit.

9. The reduced-pressure system of claim 1, further comprising:
   a reduced-pressure source; and
   a reduced-pressure delivery conduit for fluidly coupling the reduced-pressure source to the first reduced-pressure interface.

10. The reduced-pressure system of claim 9, wherein a tissue site is a first tissue site, the reduced-pressure delivery conduit is a first reduced-pressure delivery conduit and the reduced-pressure system further comprises:
    a manifold delivery tube having a passageway and a distal end, the distal end configured to be inserted into the subcutaneous delivery conduit and placed adjacent a second tissue site;
    a flowable material deliverable through the manifold delivery tube to the second tissue site such that the flowable material is capable of filling a void adjacent the second tissue site to create a manifold having a plurality of flow channels in fluid communication with the second tissue site; and
    a second reduced-pressure delivery conduit configured for fluid communication with the plurality of flow channels of the manifold.

11. The reduced-pressure system of claim 10, wherein the manifold delivery tube and the second reduced-pressure delivery conduit are the same tube.

12. The reduced-pressure system of claim 10, wherein the manifold is bioresorbable.

13. The reduced-pressure system of claim 1, wherein the second reduced-pressure interface comprises an elastomer having an aperture sized to receive a subcutaneous delivery conduit.

14. The reduced-pressure system of claim 13, wherein the second reduced-pressure interface is adapted to generate a compressive force against an outer circumference of the subcutaneous delivery conduit.

15. The reduced-pressure system of claim 1, wherein the over-drape is disposed between the dressing bolster and the second reduced-pressure interface and configured to provide a fluid seal over the dressing bolster and a portion of the epidermis.

16. The reduced-pressure system of claim 15, wherein the second reduced-pressure interface is configured to reinforce the over-drape to maintain the fluid seal around a tissue site if the over-drape is breached by the subcutaneous delivery conduit.

17. The reduced-pressure system of claim 9, further comprising a reduced-pressure indicator fluidly coupled to the reduced-pressure source.

18. A wound dressing assembly, comprising:
    a dressing bolster having a first surface and a second surface for deploying over an epidermis and comprising a plurality of flexibility notches;
    an over-drape for providing a fluid seal over the dressing bolster and a portion of the epidermis;
    a first reduced-pressure interface fluidly coupled to the dressing bolster and operable to receive a reduced-pressure supply conduit; and
    a second reduced-pressure interface, comprising an interface body formed with an aperture sized to receive a subcutaneous delivery conduit and to form a fluid seal with the subcutaneous delivery conduit.

19. The wound dressing assembly of claim 18, wherein the dressing bolster is at least partially pre-cut to allow the subcutaneous delivery conduit to pass to the second reduced-pressure interface.

20. The wound dressing assembly of claim 18, wherein the second reduced-pressure interface comprises one or more o-rings.

21. The wound dressing assembly of claim 18, further comprising an inner layer having a first surface and a second surface, formed with a treatment-area aperture, and wherein the first surface of the inner layer is coupled at least in part to the second surface of the dressing bolster.

22. The wound dressing assembly of claim 18, wherein the interface body comprises a molded elastomer.

23. The wound dressing assembly of claim 18, wherein the second reduced-pressure interface is tapered.

24. The wound dressing assembly of claim 18, wherein the dressing bolster further comprises a perforated cylinder of bolster material.

25. A method of treating a tissue site, comprising:
    applying a wound dressing assembly to the tissue site, wherein the wound dressing assembly comprises:
        a dressing bolster formed from a medical bolster material for placing on a patient's epidermis and substantially sized to overlay the tissue site,
        an over-drape for providing a fluid seal over the dressing bolster and a portion of the patient's epidermis,
        a first reduced-pressure interface fluidly coupled to the dressing bolster for delivering reduced-pressure to the dressing bolster, and
        a second reduced-pressure interface fluidly coupled to the dressing bolster and having an aperture sized to receive a conduit and to generate a compressive force against the conduit;
    fluidly coupling a reduced-pressure delivery conduit to a reduced-pressure source and the first reduced-pressure interface;
    delivering reduced pressure to the reduced-pressure delivery conduit;
    fluidly coupling a subcutaneous delivery conduit to the second reduced-pressure interface, wherein the second reduced-pressure interface is sized to transfer a hand-generated force equal to an amount of force required to puncture the over-drape with the subcutaneous delivery conduit; and
    delivering reduced pressure to the subcutaneous delivery conduit.

26. The method of treating a tissue site of claim 25, wherein the dressing bolster is pre-cut to receive the subcutaneous delivery conduit.

27. The method of treating a tissue site of claim 25, wherein the tissue site is a first tissue site and further comprising:

coupling a manifold delivery tube to the second reduced-pressure interface, the manifold delivery tube having a passageway and a distal end, the distal end configured to be inserted into the subcutaneous delivery conduit;

delivering a flowable bioresorbable material through the manifold delivery tube to a second tissue site such that the flowable bioresorbable material is capable of filling a void adjacent the second tissue site to create a manifold having a plurality of flow channels in fluid communication with the second tissue site;

coupling a reduced-pressure delivery conduit to the second reduced-pressure interface, the reduced-pressure delivery conduit capable of fluid communication with the plurality of flow channels of the manifold; and applying reduced pressure to the second tissue site.

28. The method of treating a tissue site of claim 27, wherein the manifold delivery tube and the reduced-pressure delivery conduit are the same tube.

29. The method of treating a tissue site of claim 25, wherein the second reduced-pressure interface comprises a molded elastomer.

30. The method of treating a tissue site of claim 25, further comprising inserting a sensor attached to an external diagnostic device through the second reduced-pressure interface to monitor the tissue site.

\* \* \* \* \*